United States Patent [19]

Duffy et al.

[11] 4,352,017
[45] Sep. 28, 1982

[54] APPARATUS FOR DETERMINING THE QUALITY OF A SEMICONDUCTOR SURFACE

[75] Inventors: Michael T. Duffy, Princeton Junction; John F. Corboy, Jr., Ringoes; Peter J. Zanzucchi, Lawrenceville, all of N.J.

[73] Assignee: RCA Corporation, New York, N.Y.

[21] Appl. No.: 189,356

[22] Filed: Sep. 22, 1980

[51] Int. Cl.³ .................... G01N 23/00; G01T 1/22; G01J 1/42
[52] U.S. Cl. ................. 250/358.1; 250/370; 250/372
[58] Field of Search ............ 250/358 R, 359, 360, 250/372, 370, 371; 356/51, 237

[56] References Cited

U.S. PATENT DOCUMENTS 3,451,254  6/1969  Maley ........................ 250/358
4,211,488  7/1980  Kleinknecht ................. 356/237

OTHER PUBLICATIONS

Zanzucchi, P. J. & Duffy, M. T., "Surface Damage and the Optical Reflectance of Single-Crystal Silicon", *Applied Optics,* vol. 17, No. 21, pp. 3477-3481.

Philipp, H. R. & Taft, E. A., "Optical Constants of Silicon in the Region 1-10ev," *Physical Review,* vol. 120, No. 1, Oct. 1, 1960, pp. 37-38.

*Primary Examiner*—Alfred E. Smith
*Assistant Examiner*—Janice A. Howell
*Attorney, Agent, or Firm*—Birgit E. Morris; Donald S. Cohen; Joseph D. Lazar

[57] ABSTRACT

The surface quality of a semiconductor material is determined by exposing the semiconductor surface to two light beams of different wavelengths or wavelength ranges (e.g. ultraviolet and near ultraviolet). A portion of each of the respective light beams is reflected from the semiconductor surface. The intensity of each reflected beam is measured to obtain an intensity difference whereby the magnitude of the difference is a measure of the quality of the semiconductor material.

12 Claims, 4 Drawing Figures

APPARATUS FOR DETERMINING THE QUALITY OF A SEMICONDUCTOR SURFACE

BACKGROUND OF THE INVENTION

This invention relates to apparatus for determining the crystalline quality of material of a semiconductor surface using light.

In manufacturing semiconductor devices, the surface of the semiconductor material in which the devices are fabricated must be substantially free of both physical and crystalline defects. A high degree of crystalline perfection is necessary to produce reliable devices having good electrical properties. In order to control the properties of such devices, it is necessary to be able to determine the quality of semiconductor material that is being used to make the devices.

The light reflectance of the surface of a semiconductor is generally dependent on the physical and crystallographic condition of the surface.

Physical surface damage such as scratches, pits and surface roughness, resulting from lapping and polishing procedures, can be detected by light scattering effects in the visible region of the spectrum, for example, by the use of conventional lasers to scan the semiconductor surface. Similarly, the surface texture of homoepitaxial and heteroepitaxial films, prepared on various substrates by chemical vapor deposition (CVD), can also be detected in similar fashion. An example of particular importance is silicon-on-sapphire (SOS). Surface texture of "haze", observed visually because of light scattering, has been attributed in the past to inferior quality SOS material.

Crystallographic damage (or what may be also termed "lattice disorder"), which may also result from lapping and polishing procedures or may be present in as-grown homoepitaxial or heteroepitaxial semiconductor films such as SOS, is not easily detected by reflectance methods using visible light. This is due to the fact that the well known "optical" constants of a semiconductor such as crystalline silicon are not appreciably influenced by lattice disorder in the visible region of the spectrum. However, the optical constants of silicon are significantly influenced by lattice disorder at photon energies near 4.3 eV which corresponds to the well known $X_4-X_1$ silicon transition. This transition occurs at a wavelength of about 2880 angstroms in the ultraviolet region of the spectrum. Thus, the light reflectance of silicon, which is a function of the optical constants, is sensitive to crystalline damage or lattice disorder in the UV region of the spectrum. Other semiconductors display similar reflectance properties at their corresponding characteristic wavelengths.

In copending patent application Ser. No. 189,348 entitled "A Method and Apparatus for Determining the Quality of a Semiconductor Surface," filed on Sept. 22, 1980 by M. T. Duffy and P. J. Zanzucchi, there is described a method for determining the quality of the material of a semiconductor surface. In brief, the surface quality of the semiconductor material, as described therein, is determined by exposing the semiconductor surface to two light beams of different wavelengths or wavelength ranges (e.g. ultraviolet at 2800 angstroms and near ultraviolet at 4000 angstroms). A portion of each of the respective light beams is reflected from the semiconductor surface. The intensity of each reflected beam is measured to obtain an intensity difference whereby the magnitude of the difference is a measure of the quality of the semiconductor material.

There is a need, however, for inexpensive apparatus that is capable of performing rapidly and accurately, the steps, of what is conveniently termed the "two wavelength reflectance measurement method," described in that copending application.

SUMMARY OF THE INVENTION

According to the present invention, the crystalline quality of a semiconductor is determined by apparatus for measuring the light reflectance of the semiconductor at each of two wavelengths, the difference between the respective reflectances being a measure of the crystalline quality of the semiconductor material.

BRIEF DESCRIPTION OF THE DRAWING

In the drawing:

FIG. 4 is a block schematic of a computer for use in the apparatus of FIG. 1 to automatically determine the quality of the semiconductor material.

Figure 1:
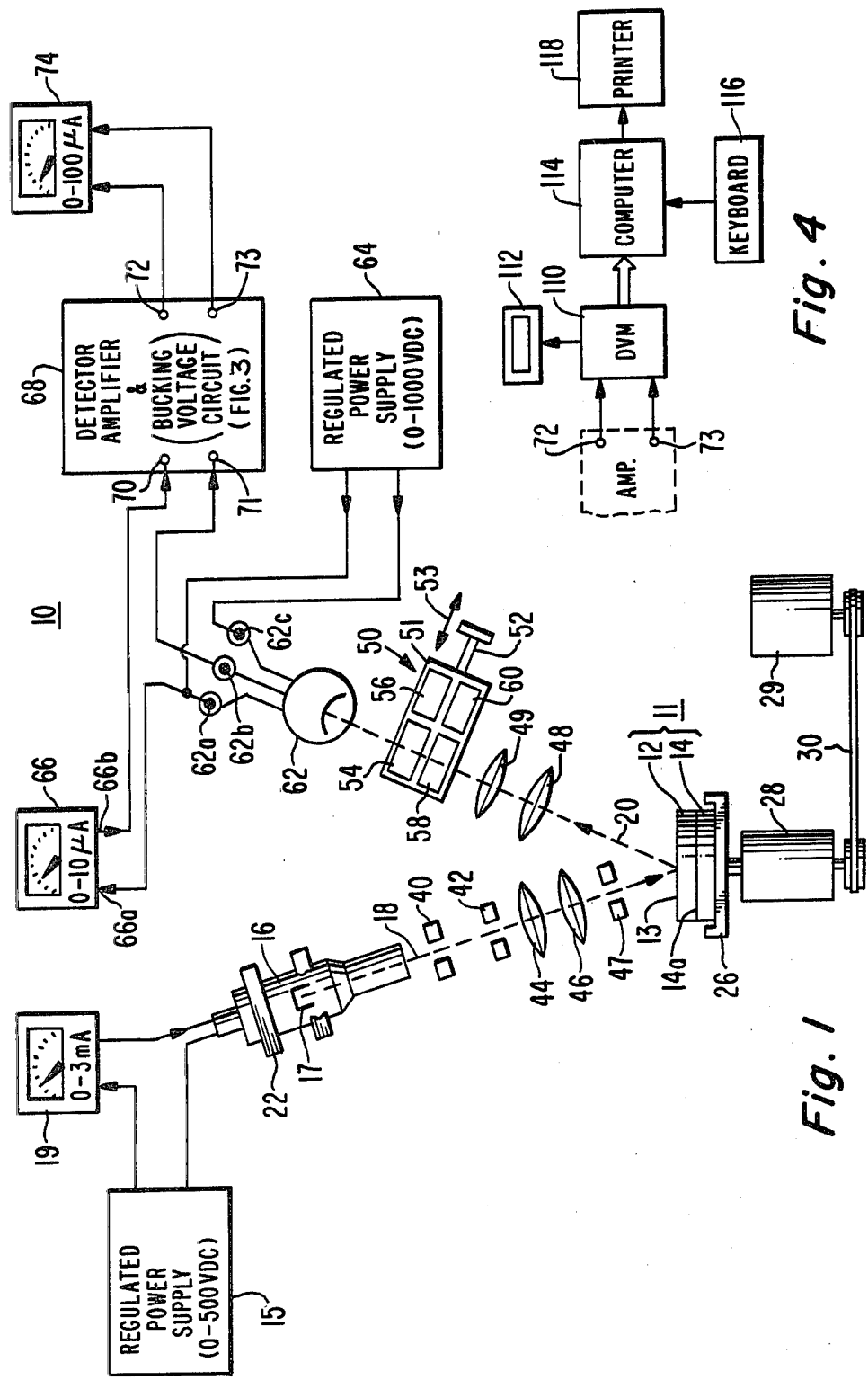
FIG. 1 is a schematic of an embodiment of the apparatus of the invention.

The present invention is based on the discovery that the magnitude of the reflectivity of heteroepitaxial silicon films at a wavelength of about 2800 angstroms can be used as a quantitative measure of the quality of SOS films for semiconductor device application. The ultraviolet (UV) reflectivity at this wavelength of about 2800 angstroms correlates very well with device parametric performance and with the results of other physical characterization methods such as x-ray analysis. The paper entitled "Surface Damage and the Optical Reflectance of Single-Crystal Silicon", published in Applied Optics, Vol. 17, No. 21, November 1978, pp. 3477-3481, describes the reflectance of silicon in the photon energy region 2.0 eV to 5.5 eV. If the crystalline perfection (i.e. quality of the crystalline structure) is degraded, the reflectance in this spectral region is decreased. In principle, the reflectance of a silicon sample relative to a standard reflector, such as an aluminum mirror, at a wavelength of about 2800 angstroms can be used to determine silicon crystalline quality provided surface physical features do not interfere with the measurement.

In practice, the use of the prior art method described in the aforementioned paper proves difficult because of wafer curvature (i.e., warpage), taper and surface texture or roughness. Moreover, a phenomenon known as "haze" in the case of silicon-on-sapphire (SOS) wafers is a commonly known problem relating to light scattering due to surface texture. These effects cause unwanted deflections and/or light scattering in the reflected light which affect the reflected intensity. Thus, the reflected intensity cannot be uniquely attributed to the degree of crystalline perfection of the sample.

According to the method described in the above-identified copending application and carried out by the apparatus of the present invention, the influence of unwanted deflections and light scattering effects on the measurement of crystalline quality is greatly diminished. By the use of two different selected wavelengths (or ranges of wavelengths) for making the reflectance measurements, the reflectance at one of the wavelengths is sensitive to both the physical and crystalline perfection of the surface while reflectance at the other wavelength (called the reference wavelength) is not as sensitive to the crystalline perfection of the surface but is nevertheless sensitive to the physical perfection of the surface. Accordingly, as shown by the curves illustrated in FIG. 2, to be further described, the reflectance of silicon at a wavelength of, for example, 2800 angstroms is decreased substantially (from about 70% to about 35%) by surface damage (both physical and crystalline) as could be caused, for example, by one micrometer diamond polishing grit while the reflectance, for example, at 4000 angstroms is not so strongly affected (i.e. from about 40% to about 35%) because it is less sensitive to crystalline damage. Accordingly, in the embodiment of this invention to be described, the reflectance of a silicon sample at about 4000 angstroms is used as a reference level with which to compare the reflectance of the same silicon sample at a wavelength in practice of about 2800 angstroms. Thus, according to the principles of the present invention, the sample itself becomes its own reference without the need for an external standard as has been heretofore considered necessary.

According to the apparatus of the present invention, both light wavelengths (or wavelength ranges) are emitted by the same source and the corresponding incident light beams subtend the same angle with respect to the same sample. Thus, both reflected beams are influenced in the same manner by the sample curvature and taper.

A preferred apparatus 10 for carrying out the invention is illustrated in FIG. 1. The apparatus 10 provides a means for testing the quality of a sample 11 formed of a semiconductor material 12 deposited on a substrate 14. Sample 11 may be bulk silicon, epitaxial layer on bulk silicon, or silicon films on sapphire or on other substrates such as glass or even metals. The surface 13 of sample 11 is exposed to a beam 18 of light from a source 16. A portion 20 of the beam 18 is reflected from the surface 13. The radiation beam 18 can be provided at either of two wavelengths in a manner to be described. In the present example, the source of light comprises a conventional hollow-cathode lamp which contains a manganese (Mn) based cathode or a conventional hydrogen light source. However, any suitable source of light 16 can be used. Source 16 is suitably supported, as by supports 22, within a housing and powered with a suitable regulated power supply 15 whose current is measured by a current meter 19 which indicates the current through the source 16. The power supply 15 suitably provides a regulated direct current voltage within the range of 0–500 volts. Meter 19 measures currents in the range of 0–3 milliamps.

The beam 18 is developed at electrode 17 and is aimed to strike the surface 13 so that a portion 20 of the beam 18 is reflected therefrom. Two wavelengths are used in the practice of the invention. Each of the wavelengths may be selected from the input beam 18 or from the reflected beam 20. In the present embodiment the wavelengths are selected from the reflected beam 20 by filter means 50 to be described. The beam 18 is collimated and focused on the surface 13 of the specimen 11 by a series of optical elements comprising a first orifice 40, a second orifice 42, a first lens 44 and a second lens 46, and a third orifice 47. The reflected beam 20 is passed through a third lens 48 and a fourth lens 49 and filtered by the filter means 50 and then falls on a detector 62.

Detector 62 is suitably a conventional photomultiplier tube having terminals 62a, 62b and 62c. Detector 62, responsive to reflected light beam 20, generates a detector d.c. output signal which can be measured on microammeter 66. The detector 62 is powered by a conventional regulated power supply 64. Detector 62 may be, if desired, a solid state detector.

The electronic signal monitoring of the detector output signal from detector 62 may be accomplished several ways. The detector output signal may be simply applied directly to meter 66. The sensitivity of such an arrangement is usually poor. The detector output signal is preferably amplified before applying the signal to a meter (or other means of display). The amplified signal can be partially offset by a bucking voltage circuit which applies a signal of opposite polarity to the meter (or display). This permits higher amplification of the detector signal while maintaining the difference signal level (between the amplified detector signal and the bucking voltage signal) within the range of the meter (or means of display). The amplification bucking voltage circuits are useful in detecting very small changes in reflectance that are difficult to monitor. Both of these techniques are illustrated in the embodiment now to be described in more detail.

As illustrated in FIG. 1, the detector output signal from detector 62 is applied to the combined detector amplifier and bucking voltage circuit 68 at terminals 70 and 71 via meter 66. Thus, terminal 62a is connected to terminal 66a of meter 66, through meter 66 to terminal 66b and thence to the detector amplifier input terminal 70. The output of circuit 68 is connected to a suitable display such as a current meter 74 via terminals 72 and 73. Meter 66 measures currents in the range of 0–10 microamperes, while meter 74 measures currents in the range of 0–100 microamperes.

Figure 3:
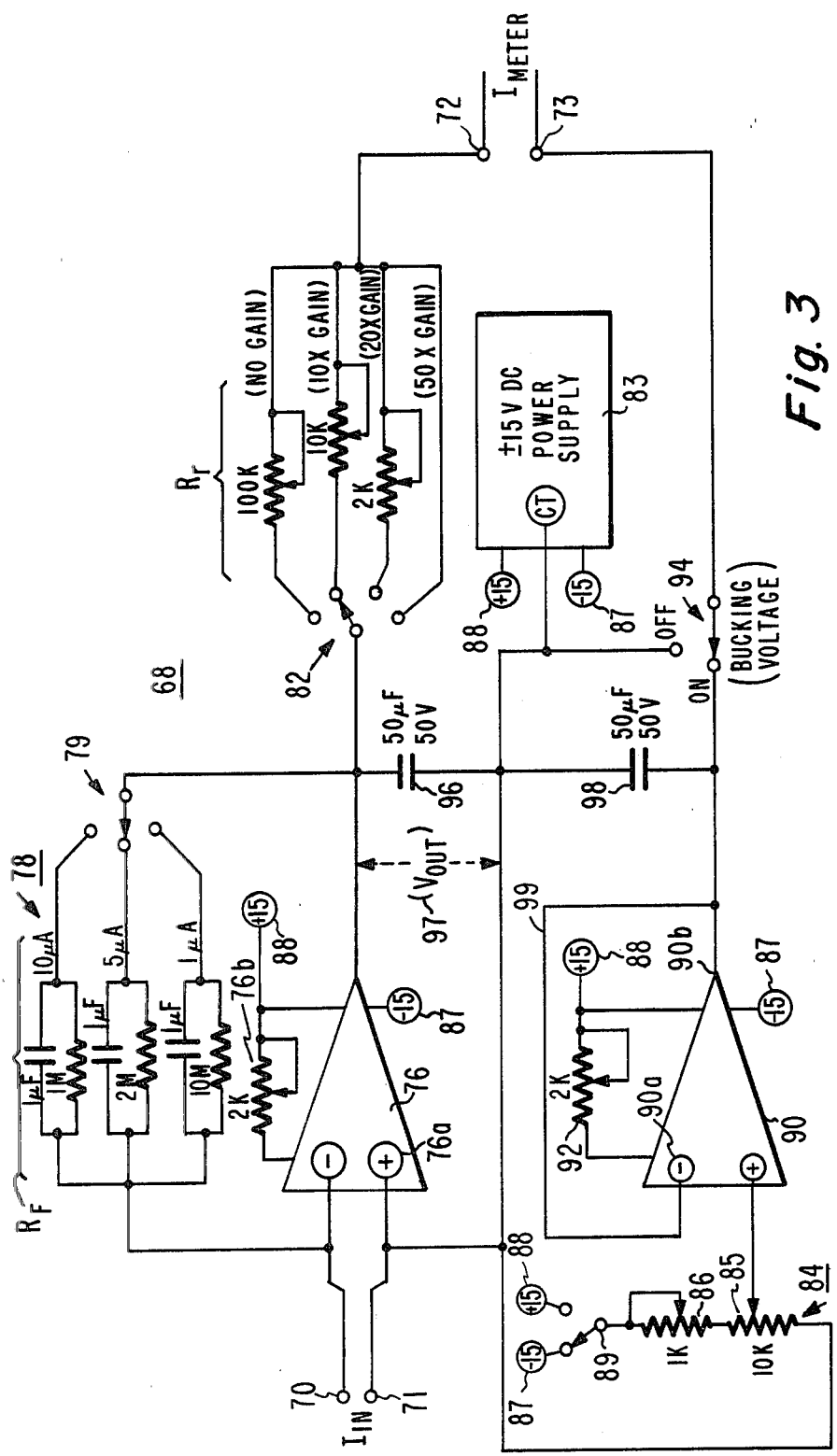
FIG. 3 is a schematic of a preferred detector amplifier and bucking voltage circuit for use in the apparatus illustrated in FIG. 1.

As shown in FIG. 3, the combined amplifier and bucking voltage circuit 68 is arranged to provide electronic monitoring of an amplifier output signal of detector 62. The input terminals 70 and 71 of circuit 68 are connected to an operational current amplifier 76 provided with a plurality of R-C networks 78 each one of which is selectable by a switch 79 to change the sensitivity range of the amplifier. The output of amplifier 76 is selectively connected to any one of a group of adjustable attenuators 80, each comprising a potentiometer via a switch 82 for selecting the desired attenuation. The attenuators 80 are commonly connected to output terminal 72. Op-amp 76 (as well as op-amp 90 to be described) is suitably a junction type FET amplifier such a Teledyne type JFET 1021. A conventional potentiometer 76b is provided for output adjustments.

The positive input terminal 76a of operational amplifier 76 is connected to the common terminal (CT) of d.c. power supply 83 and to one terminal of an adjustable bias 84 comprising a first potentiometer 85 and a second potentiometer 86. The second potentiometer 86 is selectably connected alternatively to negative 15 voltage source 87 of supply 83 or a positive voltage source 88 via switch 89. The wiper arm of first potentiometer 85 is connected to the positive terminal of operational current amplifier 90 having a trim and potentiometer adjustment 92 to adjust the output. The output of amplifier 90 is applied to terminal 73 via closed single-pole double-throw switch 94. In the closed ("on") position, switch 94 places the circuit 68 in the bucking voltage mode to be described further below.

When switch 94 is in the "off" position, the circuit 68 functions merely to amplify the detector (62) output signal for application to the meter 74. The four position, single pole switch 82 is operated to provide the desired attenuation. Switch 79, a three position single-pole switch, is operated to connect the appropriate network 78 into the circuit and switch 94 is operated to the "off" position. With this arrangement of the circuit of FIG. 3, the detector output signal is amplified and applied to the meter 74 without a bucking voltage.

The use of amplifier 76 at high gain for increased resolution would cause meter 74 to go off scale of a 100 microamp meter, for example. Accordingly, by providing a bucking voltage to compensate or offset in part the amplified detector output signal greater amplification can be used for the detector signal, thereby increasing significantly the resolution of the reflectance measurements. This is accomplished with the amplifier 90 placed in operation in the circuit by switch 94 in the "on" position. Potentiometers 85 and 86 are adjusted to provide a voltage at the positive input terminal of amplifier 90 with a polarity depending upon the position of switch 89. It should be appreciated that the polarity of the output of op-amp 90 depends on the polarity of the input to op-amp 76. If the input to op-amp 76 is reversed to that shown, switch 89 is positioned to +15 V at terminal 88. Furthermore, the polarity of meter 74 will be suitably reversed as by a reversing switch.

The output voltage 97 ($V_{out}$) from amplifier 76 is applied across capacitor 96. Another capacitor 98 is connected between one terminal of potentiometer 85 and the output terminal 90b of op-amp 90 which is also connected to the negative terminal 90a of op-amp 90 via lead 99. Thus, the op-amp 90 provides an output signal that is fed back to its negative input terminal 90a. The output of the amplifier 90 is adjustable by varying the potentiometer 84.

The output voltage 97 from op-amp 76 is determined from the following relation:

$$V_{out} = I_{in} \times R_f \qquad (1)$$

where $I_{in}$ in the current input to op-amp 76 from detector 62 (via meter 66) and $R_f$ is the resistance of the selected feedback R-C network 78. The current output from circuit 68 ($I_{meter}$) which is applied to meter 74 is $$I_{meter} = V_{out}/(R_r + R_{meter}) \qquad (2)$$

where $V_{out}$ is determined from equation (1), $R_r$ the resistance of one of the selected potentiometers 80 and $R_{meter}$ is the resistance of the meter 74.

The circuit 68 of FIG. 3 when placed in the bucking voltage mode by switch 94 in the "on" position provides a current from op-amp 90 through meter 74 which is opposite in polarity to the current through 74 from op-amp 76. By offsetting the output from op-amp 76, a greater degree of amplification of the detector (62) output signal can be provided by op-amp 76 without causing the reading on meter 74 to go off scale. Thus, the apparatus provides enhanced resolution for low level signals from detector 62.

Filter means 50 is formed of optical filters 54 and 56 suitably supported within a frame 51 for selectable positioning in the path of either of the beams 18 or 20 by a handle 52 operated to move the filters in either of the two directions shown by arrows 53. As shown in FIG. 1, the filter means 50 is preferably arranged to be positioned in the path of the reflected light beam 20. Filter 54 passes ultraviolet light at about 2800 angstroms when the apparatus is used to test a specimen 11 formed of silicon material (12). For such a test, filter 56 is selected to pass light at a wavelength of about 4000 angstroms. Other filters 54 and 56 could be provided to pass light at other wavelengths depending upon the material chosen to be tested.

Filters 58 and 60 are provided on an optional basis when it is desired to operate the apparatus in a different mode as will be described further hereinafter.

In operation of the apparatus 10, the specimen 11 is placed on stage 26. The stage 26 is rotated by motor 29 and belt 30 which in turn rotates shaft 28. The shaft 28 supports the stage 26 which will rotate it as the shaft rotates. By changing the position of stage 26 relative to the incident light 18 and by rotation of shaft 28, one can illuminate in sequence a plurality of different portions of surface 13 for each series of tests. Beam 18 is arranged to provide a sampling spot size on the surface 13 of the specimen in the range of 1-5 mm.

The surface 13 is illuminated by the beam 18 and the reflected beam 20, after being focused by lens 48 and 49, is passed through either filter 54 or 56 and then onto detector 62. Filter means 50 is adjusted to provide light at, for example, 4000 angstroms for one measurement and at 2800 angstroms for the second measurement in accordance with the requirements of equations (3) or (4) to be described. Detector 62, responsive to reflected signals 20 at the two respective wavelengths determined by filters 54 and 56, provides a detector output signal which is amplified and displayed on either meter 66 and 74.

Figure 2:
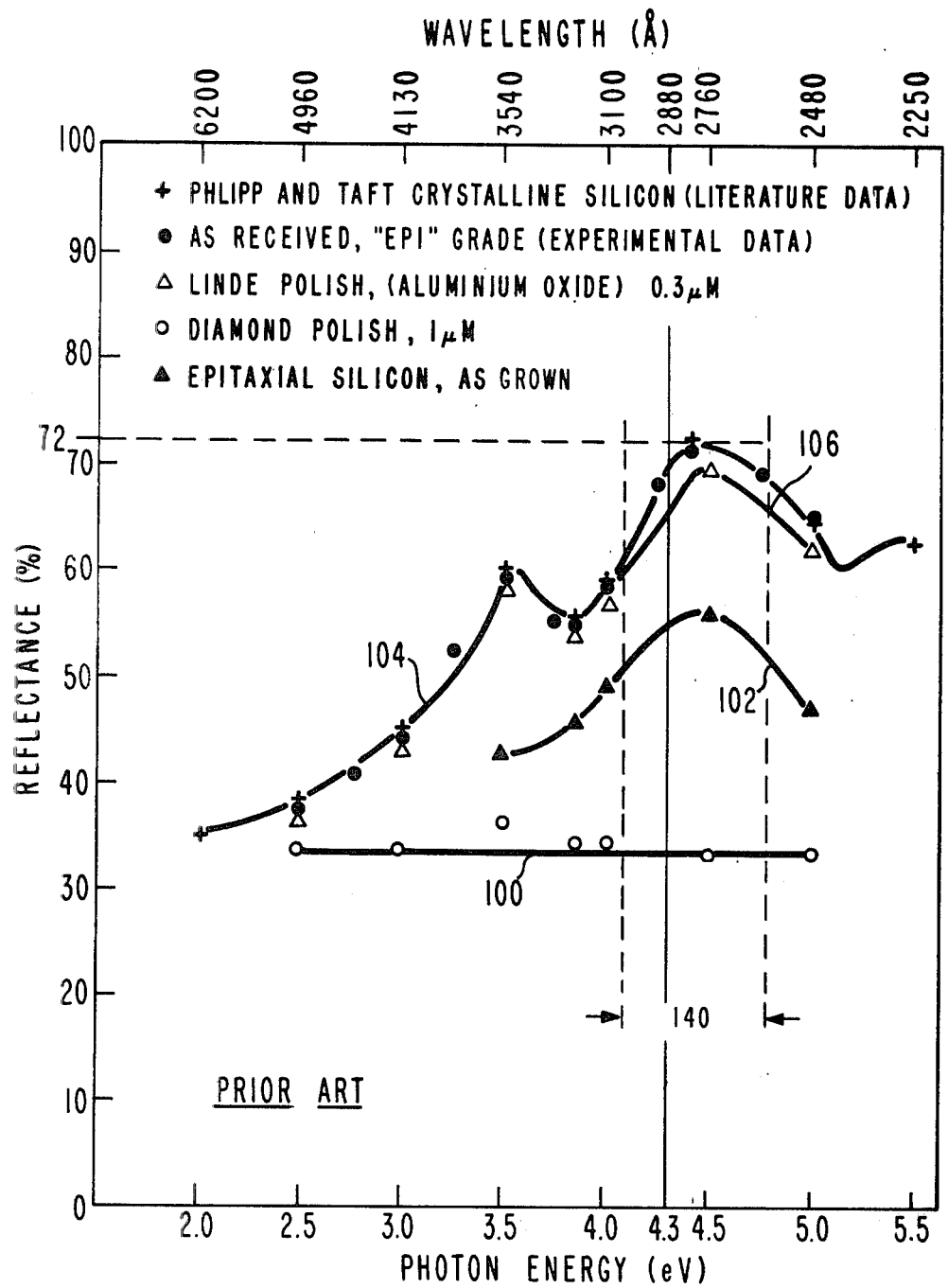
FIG. 2 are curve plots useful in understanding the invention illustrating the reflectance of a single-crystal silicon surface as a function of the photon energy eV and the corresponding wavelength of the incident radiation.

The measured current is at a maximum when the reflectance is maximum as indicated by the region 140 of response curve 104 shown in FIG. 2 to be described. Then, the current measured at about 4000 angstroms provides a means to determine the difference of the reflectances measured. The reflected radiations at both wavelengths is modified by the sample curvature or warpage and taper in the same manner. Accordingly, the difference in reflectance ($\Delta R$) at the two wavelengths (or wavelength ranges) is equal to $$A - B = \Delta R \qquad (3)$$

and is a measure of crystalline quality for the sample being measured, wherein A is the reflectance for light at 2800 angstroms and B is the reflectance of light at 4000 angstroms, in the case of silicon. The difference in reflectance ($\Delta R$) for a well polished silicon wafer of high crystalline quality can be used to determine the level of perfection attainable. It should be noted, however, that light scattering due to surface roughness or "haze" is a function of wavelength. Since two different wavelengths are involved, the value of $\Delta R$ is also modified by surface roughness or "haze" but not nearly so strongly as the measured intensity at either wavelength. Accordingly, the influence of surface roughness on the determination of crystalline quality is greatly diminished.

There are several ways in which the reflectance at the two wavelengths might be compared to each other. For example, the value of ΔR might be normalized according to the following expression;

$$\Delta R' = (A-B)/(B) \quad (4)$$

wherein A and B are the reflectances as defined above for equation (3) and ΔR'=(ΔR)/(B). The values of the two wavelengths selected for the characterization of a silicon sample can be different from the specific values of 2800 angstroms and 4000 angstroms as discussed above. However, for evaluation of silicon films on sapphire, the reference wavelength should not be greater than about 4000 angstroms because some light penetrating the silicon film 12 at the selected reference wavelength may be reflected at the surface 14a of the sapphire and cause unwanted light interference effects in the specularly reflected light. This phenomenon depends upon the thickness of the silicon film used. Note that the reference wavelength could be less than 4000 angstroms. Moreover, in the evaluation of polished silicon wafers, the reference wavelength can be greater than 4000 angstroms since interference effects do not occur. The reference wavelength could also be chosen at shorter wavelengths than 2800 angstroms, for example 2000 angstroms, for the evaluation of silicon. The penetration depth for radiation at a wavelength of about 2800 angstroms is limited to a surface layer of silicon which may be as thin as about 100 angstroms or less. Consequently, the light reflectance technique according to the present invention for the characterization of silicon is related principally to a shallow surface layer of material of about 50 angstroms in thickness.

The apparatus as described above provides a means for making relative reflectance measurements with the measured intensity at about 4000 angstroms (when testing silicon material) forming the reference level for comparison with the reflectance at about 2800 angstroms. The difference in the measured intensity at the two wavelengths can be used as a crystalline quality "figure-of-merit" for the unknown sample (11) with the understanding that, as the surface 13 has some roughness, there is some dependence on the difference in reflectance (ΔR or ΔR') on the degrees of roughness, but much less than if a measurement is made at either wavelength (or wavelength range).

The sample being evaluated becomes its own reference in that the measurement does not depend on an external reference reflector. Nevertheless, measurements on a known sample of "good" properties can be used as a basis for determining the level of perfection attainable, but it should be understood that it is not essential to the evaluation of an unknown sample. The larger the values of ΔR and ΔR' the better the quality of the sample being evaluated. For well polished silicon, the value of ΔR is about 0.22 and the value of ΔR' is about 0.46. Smaller values than these represent inferior quality silicon.

Another mode of operation of apparatus 10 will now be described. For practical reasons it is desirable to operate the apparatus in a mode which will allow for periodic calibration of the instrumentation. This is accomplished in the following manner. A well-polished silicon wafer is placed on sample holder 26 to serve as a reference reflector. Suitable neutral density filters 58 and 60 are selected and arranged preferably in front of (or back of) optical filters 54 and 56, respectively, so that the output signals, from detector 62, corresponding to the wavelengths 2800 angstroms and 4000 angstroms, are respectively attenuated to be equal as displayed on microammeters 66 and 74. The light intensity from source 16 is adjusted to give a predetermined signal level on meter 66, for example, 2 μA. The bucking-voltage from amplifier 90 is adjusted so that full-scale deflection is obtained on meter 74 at the desired resolution level. When an unknown sample 11 is subsequently used as a reflector, any difference in reflectance as indicated by meters 66 and 74 can be attributed to the departure of sample quality from that of the reference reflector, namely, the silicon wafer.

This procedure can be used on a routine basis for calibrating the apparatus 10. Such a procedure is desirable to offset changes which may occur with time in the components of the apparatus. For example, light source 16 can change its output over a period of time in operation. In operating the equipment with the reference polished silicon, it should be understood that the values of the terms ΔR and ΔR' are both zero. These terms become negative quantities in the case of inferior quality silicon. The negative quantities result from the fact that the value of reflectance at 2800 angstroms decreases more rapidly than the value of reflectance at 4000 angstroms if the silicon quality is degraded. It is convenient to take the numerical (or absolute) values of the terms ΔR and ΔR', when the apparatus is used in this mode of using a polished silicon reference to calibrate the apparatus. In such a mode of operation, small values of the numerical quantities of these terms represent "good" quality silicon and larger values represent "poor" quality silicon.

A still further modification of the apparatus may be made to monitor the electronic output signals from detector 62. In this modification, the radiation from the light source 16 may be chopped either before or after reflection from the sample 11 and phase sensitive detection used to measure the signal output electronically. Such chopping techniques are well known in optical detection methods and will not be described in detail.

In the present embodiment of the invention being described, the respective reflectances measured for the two wavelengths is done in accordance with equation (3) in the characterization of single crystalline material an equation (4) in the case of polycrystalline or amorphous material described hereinabove. Nevertheless, it will be appreciated that the respective reflectances can be, for example, related as ratios rather than arithmetic differences as exemplified by equations (1) and (2).

As shown in FIG. 2, the reflectance characteristics as "reflectance (%)" plotted both against the photon energy (eV) (bottom axis) and the wavelength of reflected signals corresponding to photon energy (top axis) makes clear how the reflectance varies with each of those related parameters. These curve plots (FIG. 2) first disclosed in the above-identified "Applied Optics" paper, will be used in the discussion to follow. Curve 100 represents the reflectance from a silicon wafer that has been polished with diamond. Note that the reflectance for curve 100 is substantially constant. Thus, there is no dependence of reflectance on wavelength in the region of photon energies between 2.5 and 5 eV. Curve 102 is a plot of the reflectance characteristics of the surface of expitaxial silicon as grown by an expitaxial process. It will be noticed that curve 102 starts with a reflectance of about 40% at 3.5 eV and peaks at about 55% near 4.5 eV and then drops off at about 45% as it approaches 5.0 eV. Curve 104 is a plot of data from several sources. It includes literature data as reported by Phillip and Taft determining the reflectivity characteristics of crystalline silicon. The solid dots of curve 104 are the experimental data determined experimentally as explained in the above-identified article "Applied Optics", Vol. 17. Curve 106 represents experimental results on the reflectivity of silicon that has been polished with a type of aluminum oxide known as Linde polish in which the grit size of the aluminum oxide is 0.3 microns. Curve 106 displays diminished reflectance due to polishing damage particularly in the region near 2800 angstroms. What should be noticed in regard of the curves 100, 102, 104 and 106 is that along the substantially common ordinate around 4.5 eV within the region 140 there is a difference in the reflectance that manifests different degrees of discernable damage.

In the embodiment of the invention being described, the evaluation of single crystal silicon has been done in experiments primarily in accordance with equation (3) with the calibration procedure described above. However, equation (4) has also been used in the evaluation of polycrystalline and amorphous silicon, in addition to evaluating single crystal silicon.

The comparison required to determine the respective reflectances is determined by comparing the magnitude of the respective currents indicated on the meter 66 or 74 at each of the two selected wavelengths determined by filters 54, 56, 58 and 60. The reflectance characteristics plotted against the photon energy (eV) and corresponding wavelength of reflected signals makes clear how the reflectance of silicon varies with the wavelength and the corresponding photon energy of the reflected light.

The reflectance curve 104 for silicon in FIG. 2 increases from about 35% reflectance at about 2.0 eV to a maximum of about 72% at a photon energy of 4.5 eV. Other semiconductors have similar characteristic curves. The photon energy in electron volts (eV) is related to the corresponding wavelength of light by the relationship $$\epsilon\lambda = hc = 1.24 \quad (5)$$

where $\epsilon$ is the photon energy in eV (electron volts), $\lambda$ is the wavelength in micrometers, h is Planck's constant and c is the velocity of light.

In the plots in FIG. 2 of the reflectance characteristics for silicon, we have observed that reflectance in the spectral region centered at about 2800 angstroms, designated region 140 for convenience, is diminished due to surface damage and inferior surface crystalline quality as demonstrated for the case of 1 $\mu$m diamond grit abrasion (curve 100) and also in the case of "as-grown" epitaxial silicon (curve 102). The ultra-violet reflectance of silicon measured in region 140, it should be understood, gives information very different from reflectance measured in the visible region of the spectrum such as measured by commercial laser scanners. Similar considerations apply to optical reflectance methods on semiconductor materials other than silicon. For example, the region 140 of a similar but relevant curve 104 for germanium is centered at about 4.5 eV which corresponds to UV radiation having a wavelength of about 2760 angstroms. For gallium arsenide, region 140 is centered about 5.0 eV for a UV wavelength of about 2480 angstroms. In the case of both germanium and gallium arsenide it is expected that light at 4000 angstroms will serve as an adequate reference. Further investigations of these semiconductors may point to a better reference wavelength of light.

In the basic form of apparatus for practicing the invention the detected intensity sinals are suitably amplified and displayed by an analogue d.c. meter coupled to the amplifier. The preferred way of providing enhanced resolution of the respective detected intensity signals at the two light wavelengths is by the use of an amplifier and bucking voltage circuit with zero-offset calibrating means illustrated in FIG. 3 described above. However, adequate resolution can be achieved by a digital voltmeter instead of the analogue meter 74. Since digital meters display an output signal that is accurate to many significant places, zero offsetting to achieve good resolution is not needed. However, digital voltmeters are quite costly and therefore are not preferred.

Means can be provided for automatically determining the quality of the semiconductor material using a computer as shown in FIG. 4. The d.c. analgoue voltage output generated at terminals 72 and 73 of amplifier circuit 68, with bucking voltage switch 94 in the "off" position, is applied to a digital voltmeter (DVM) 110. DVM 110 has a display 112 indicating the output signal $I_{meter}$. DVM 110 provides an output signal representing each analogue signal in digital form for use by computer 114. A keyboard 116 coupled to computer 114 is used to provide manual input data to associate the tested specimens with the computations to be made. Computer 114 under control of keyboard 116 responds to each intensity signal to store them for subsequent comparison and computation of $\Delta R$ or $\Delta R'$. If desired, lookup tables are provided to provide a figure of merit or quality of the semiconductor instead of a numerical value of $\Delta R$ or $\Delta R'$. A printer 118 provides a print out of the desired data.

Using the apparatus of the present invention as described above, one can determine the crystalline quality of the semiconductors. Reduced reflectance is in all cases related to reduced surface physical perfection and reduced surface crystalline perfection and these two latter properties can be largely separated by the two-wavelength measurement apparatus according to this invention using appropriate wavelengths for each semiconductor. The present invention lends itself to a nondestructive, fast, simple and sensitive means for determining the quality of a semiconductor material. The semiconductor surface can be evaluated for crystalline quality prior to the manufacture of devices, thereby eliminating the costly continuation of device processing in inferior semiconductor material. In particular, it can be used for bulk silicon, homoepitaxial silicon or heteroepitaxial silicon and, at relevant wavelengths, the technique can be used to evaluate the surface quality of semiconductor materials other than silicon, such as germanium and gallium arsenide.

What is claimed is:

1. Apparatus for determining the surface quality of a semiconductor material comprising:
    (a) means for exposing said semiconductor surface to a first beam of radiation of a first wavelength from a source of radiation at a preselected angle of incidence so that a portion of said first beam is reflected from said surface;
    (b) means for exposing thereafter said semiconductor surface to a second beam of radiation from said source at said angle having a second wavelength different from said first radiation so that a portion of said second beam is reflected from said surface, the wavelength of one of said beams being in the ultra-violet spectrum region wherein the influence of crystal lattice disorder of the material on reflectance is significantly greater than the influence of crystal lattice disorder on reflectance of said material at the other wavelength;

(c) means for determining, in sequence, the intensity respectively, of the first reflected beam to obtain a first intensity signal, and of the second reflected beam to obtain a second intensity signal;

(d) means for comparing said first intensity signal with said second intensity signal to provide information indicative of the difference between the first and second intensity signals, the difference between said signals being a measure of quality of said semiconductor material; and (e) means for providing sufficient resolution for comparing very small differences in said first and second intensity signals.

2. The apparatus of claim 1 wherein the intensity determining means includes a light detector responsive to each of the radiating beams for generating an electrical signal representing the intensity of each of the respective beam and display means responsive to each of the intensity signals for providing visual indica of the beam intensity of each of the respective beams.

3. The apparatus of claim 2 further comprising amplifying means including a first amplifier responding to said detector signal for providing an amplified detector signal to said display means and wherein said resolution increasing means inclues a second amplifier having an adjustable input means to adjust the output signal of the second amplifier to a predetermined value equal to one of said amplified detector signals, and means coupling said amplified detector signal in opposite polarity to said second amplifier signal so that the signal applied to the display means is the difference between the amplified detector signal and the second amplifier signal.

4. The apparatus of claim 1 wherein the first and second wavelength exposing means includes a selectable optical filter means for filtering said first and second beams to provide light at preselected wavelengths.

5. The apparatus of claim 2 further including means to calibrate said apparatus with respect to a given reference specimen of semiconductor material, said calibration means including selectable neutral density optical filter means to attenuate the respective intensities of the first and second beams to values such that the respective detector signals are equal whereby the difference in detector signals obtained for the first and second beams reflected from an unknown sample of semiconductor material is a measure of the quality of said sample and a measure of the departure of the unknown sample from the quality of the reference specimen.

6. The apparatus of claim 5 wherein said calibration means further includes means for adjusting the intensity of radiation of the beams to obtain a predetermined detector signal out.

7. The apparatus of claim 1 further including means for positioning the specimen so that different portions of the surface can be sequentially exposed to said first and second beams.

8. The apparatus of claim 1 wherein the first beam has a wavelength substantially equal to the wavelength at which reflectance is maximum for the particular semiconductor material being evaluated.

9. The apparatus of claim 1 wherein the material is silicon and wherein said exposing means includes means for exposing the silicon to the first beam at about 2800 angstroms and to the second beam at about 4000 angstroms.

10. The apparatus of claim 1 wherein said determining means includes an analogue d.c. meter.

11. The apparatus of claim 1 wherein said determining means includes a digital voltmeter.

12. The apparatus of claim 1 wherein said comparison means includes a digital computer for calculating the difference between the first and second intensity signals.

* * * * *